(12) United States Patent
Lee et al.

(10) Patent No.: US 11,192,864 B2
(45) Date of Patent: Dec. 7, 2021

(54) METHOD FOR PRODUCING CALCOBUTROL

(71) Applicant: ENZYCHEM LIFESCIENCES CORPORATION, Jecheon-si (KR)

(72) Inventors: Jae Yong Lee, Yongin-si (KR); Jong Soo Lee, Wonju-si (KR); Byung Kyu Kang, Jecheon-si (KR); Byuong Woo Lee, Jecheon-si (KR); Sang Oh Lee, Daejeon (KR); Dae Myoung Yun, Wonju-si (KR); Jae Hun Bang, Daegu (KR); Ki Young Sohn, Seoul (KR)

(73) Assignee: ENZYCHEM LIFESCIENCES CORPORATION, Jecheon-si (KR)

( * ) Notice: Subject to any disclaimer, the term of this patent is extended or adjusted under 35 U.S.C. 154(b) by 0 days.

(21) Appl. No.: 16/962,287

(22) PCT Filed: Jan. 11, 2019

(86) PCT No.: PCT/KR2019/000484
§ 371 (c)(1),
(2) Date: Jul. 15, 2020

(87) PCT Pub. No.: WO2019/143074
PCT Pub. Date: Jul. 25, 2019

(65) Prior Publication Data
US 2020/0385358 A1 Dec. 10, 2020

(30) Foreign Application Priority Data
Jan. 19, 2018 (KR) .................. KR10-2018-0007311

(51) Int. Cl.
*C07D 257/02* (2006.01)
*A61K 49/10* (2006.01)

(52) U.S. Cl.
CPC ............ *C07D 257/02* (2013.01); *A61K 49/10* (2013.01)

(58) Field of Classification Search
CPC .............................. C07D 257/02; A61K 49/10
USPC ........................................................... 540/470
See application file for complete search history.

(56) References Cited

U.S. PATENT DOCUMENTS

2011/0028431 A1    2/2011  Zerbe et al.
2012/0309962 A1*  12/2012  Platzek ................ C07D 257/02
                                                              540/474

FOREIGN PATENT DOCUMENTS

| CN | 106187930 | 12/2016 |
| KR | 10-2012-0093388 | 8/2012 |
| KR | 10-2013-0089229 | 8/2013 |
| KR | 10-2016-0032872 | 3/2016 |

OTHER PUBLICATIONS

KIPO, PCT International Preliminary Report on Patentability of PCT/KR2019/000484 dated Jul. 21, 2020.
KIPO, PCT Written Opinion of PCT/KR2019/000484 dated Apr. 25, 2019.

* cited by examiner

*Primary Examiner* — Rita J Desai
(74) *Attorney, Agent, or Firm* — Lex IP Meister, PLLC

(57) ABSTRACT

Disclosed is a method for producing calcobutrol used as an MRI contrast agent. The method comprises the steps of: obtaining butrol represented by chemical formula 2 in the specification by reacting a gadobutrol represented by chemical formula 1 in the specification and a decomplexing agent; and obtaining a calcobutrol represented by chemical Formula 3 in the specification by reacting butrol with calcium ions.

2 Claims, No Drawings

METHOD FOR PRODUCING CALCOBUTROL

FIELD OF INVENTION

The present invention relates to a method for producing calcobutrol, and more particularly, to a method for producing calcobutrol used in an MRI contrast agent.

BACKGROUND OF INVENTION

Gadobutrol is marketed worldwide under the trade name Gadovist or Gadavist in the field of gadolinium-containing contrast agents).

It has been found that for gadolinium-containing contrast agents it is advantage to apply an excess of the complex-forming ligand in the form of the calcium complex. The role of the calcium complex is to prevent the release of free gadolinium in the formulation from gadobutrol after the preparation, thereby solving the safety issue against nephrogenic systemic fibrosis (NSF) caused by the toxicity of gadolinium cations.

The synthesis method of calcobutrol is described in detail in the literature (Inorg. Chem. 1997, 36, 6086~6093). A material having a purity of 90~95% is obtained by the method of the document, but it does not reach the purity required for preparation.

For further purification of 2,2,2-(10-1,3,4-trihydroxybutan-2-yl)-1,4,7,10-tetraazacyclododecane-1,4,7-triyl)triacetic acid (hereinafter referred to as 'butrol'), it is not easy to purify with ion exchange resin due to zwitterionic of butrol and also crystallization through pH adjustment is not made so purification by crystallization is also not possible.

Gadobutrol, a neutral gadolinium complex, can be obtained with high purity (>99.6%) through purification and crystallization after reaction with an ion exchange column, but calcobutrol has a problem that it is not easy to purify due to the remaining acid functional groups. Therefore, it is known that a method for manufacturing calcobutrol directly from butrol is not suitable in terms of purity.

According to Korean Patent No. 10-1057939 owned by Bayer pharma aktiengesellschaft, a method for manufacturing high purity calcobutrol is known as follows: the previously obtained gadobutrol is selected as a starting material and decomplexed, and free gadolinium is removed to prepare high purity butrol and then the butrol is complexed with calcium to prepare calcobutrol. However, the oxalic acid used for decomplexation in the above method is toxic and has limitations in use. Also, other impurities are removed through the process of adsorbing and desorbing butrol to the cation exchange resin to produce high purity butrol, which then is reacted with calcium ions to obtain calcobutrol. But, these series of processes are not economical and the processes are also complicated.

According to the Korean Patent No. 10-1693400 owned by ST Pharm Co., Ltd., a method for manufacturing calcobutrol is known as follows: 3-(1,4,7,10-tetraazacyclododecan-1-yl)butane-1,2,4-triol 4 hydrochloride, an intermediate of gadobutrol is the starting material, and tert-butylbromoacetate is introduced, then which is subject to the deprotection process; then high purity butrol is obtained through resin purification and it is reacted with calcium ions to obtain calcobutrol. However, the tert-butylbromoacetate used in the above method is harmful to the human body, and has a disadvantage in that the price is very expensive. Also, the deprotection process is not economical, and the process is complicated.

Accordingly, there is a need to develop a method for manufacturing a high purity calcobutrol less harmful to the human body, eco-friendly, economical and simple by excluding the resin purification and deprotection process.

SUMMARY OF THE INVENTION

Accordingly, it is an object of the present invention to provide a method for producing calcobutrol having a higher purity than a process using butrol, an intermediate of gadobutrol.

It is another object of the present invention to provide a method for producing a calcobutrol which is simpler and more economical than a method for producing a known high purity gadobutrol as a starting material.

To achieve these objects, this invention provides a method for producing calcobutrol comprising the steps of: obtaining butrol represented by the following Chemical Formula 2 by reacting a gadobutrol represented by the following Chemical Formula 1 and a decomplexing agent; and reacting calcium ions with the butrol to obtain a calcobutrol represented by the following Chemical Formula 3.

As described above, the method for producing calcobutrol according to the present invention is simpler and more economical than the conventional method for producing calcobutrol using a high purity gadobutrol as a starting material.

DETAILED DESCRIPTION OF INVENTION

Hereinafter, the present invention will be described in more detail.

In order to prepare butrol according to the present invention, first, the gadolinium complex of 2,2,2-(10-1,3,4-trihydroxybutan-2-yl)-1,4,7,10-tetraazacyclododecane-1,4,7-triyl)acetic acid (hereinafter, gadobutrol) represented by the following Chemical Formula 1, a starting material is reacted with a decomplexing agent to obtain 2,2,2-(10-1,3,4-trihydroxybutan-2-yl)-1,4,7,10-tetraazacyclododecane-1,4,7-triyl)triacetic acid (hereinafter referred to as butrol) represented by the following Chemical Formula 2.

[Chemical Formula 1]

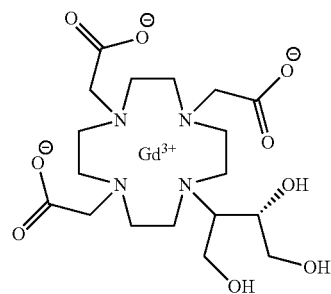

[Chemical Formula 2]

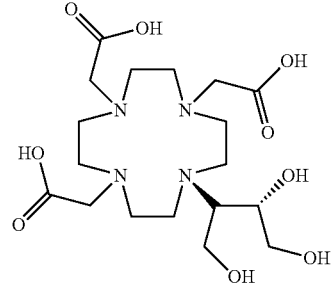

The decomplexing agent de-complexes gadolinium of gadobutrol to form a gadolinium salt that is poorly soluble in water, so that butrol can be isolated through a filtration process. The decomplexing agent includes tartaric acid, succinic acid, citric acid, fumaric acid, and so on, preferably tartaric acid is preferred. The content of the decomplexing agent is 2.0 to 6.0 equivalents, preferably is 3.0 to 4.0 equivalents, with respect to 1.0 equivalent of gadobutrol. If the content of the decomplexing agent is too less, not only the reactivity is poor and the reaction time is long, but also it may be a problem in yield and quality due to the generation of a related substance by heat. If the content of the decomplexing agent is too high, the cost of removing the decomplexing agent remaining after the reaction is further incurred, causing a cost increase.

The reaction can be carried out in purified water, and the reaction temperature is generally 80 to 90° C. If the reaction temperature is too low, it causes a rise in cost due to a time delay, and if it is too high, a quality problem may occur. The reaction time is 3 to 5 hours. If the reaction time is too short, the yield due to unreacted products may decrease, and if it is too long, there is no economical benefit from working time increasing.

The salt prepared from the reaction is filtering and separated and the filtrate is again filtered, so that the remaining decomplexing agent and by-products may be removed. Concentrating the purified filtrate removes gadolinium from gadobutrol to obtain a butrol.

Specifically, it is filtered using a nano filter. The nano-filter system has a spiral shape of an organic film and a reverse osmosis device designed to filter or concentrate substances with a molar mass of 200 to 300 Daltons or more, so that water-soluble organic or inorganic materials with salts and other low molecular weights can be separated and purified through the organic film to recover only the desired material.

2,2,2-(10-1,3,4-trihydroxybutan-2-yl)-1,4,7,10-tetraazacyclododecane-1,4,7-triyl) triacetate calcium complex (hereinafter, calcobutrol) represented by the following Chemical Formula 3 is obtained by reacting the butrol represented by the following Chemical Formula 2 with a calcium ions, and crystallizing the same.

[Chemical Formula 3]

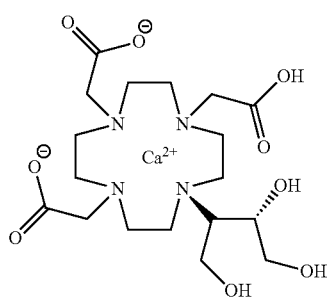

The reaction can be carried out in purified water. The source of calcium ions includes calcium carbonate, calcium hydroxide, calcium chloride, and so on, and calcium carbonate is preferred. The content of the calcium ion source is 0.9 to 1.1 equivalents, preferably is 1.0 equivalent, with respect to 1.0 equivalent of butrol. Here, if the content of the calcium source is too less, the complex is less formed, yield reduction occurs, and if too large, there is a problem in that the filtering of the remaining calcium carbonate is difficult.

The reaction temperature is generally 85 to 95° C. If the reaction temperature is too low, there is a decrease in yield due to unreacted substances, and if it is too high, related substances can occur and product quality problems can occur. Also, the reaction time of the butrol and calcium ion is 2 to 3 hours. If the reaction time is too short, a problem may occur in yield reduction and crystallization due to unreacted materials. If the reaction time is too long, a problem may occur in the quality of the product.

The reactants can be filtered on an activated carbon pad and the filtrate is concentrated, dissolved in purified water, crystallized and isolated with anhydrous ethanol. As the crystallization solvent an organic solvent such as anhydrous ethanol, methanol, isopropanol, acetone and so on can be used, and anhydrous ethanol is preferred. Specifically, the filtrate can be crystallized under purified water-anhydrous ethanol conditions at generally 60 to 80° C. Therefore, when the crystallized mixture is dried, calcobutrol can be obtained.

EXAMPLES

Hereinafter, the present invention is described in more detail through examples, but the present invention is not limited by the following examples.

[Example 1] Preparation of Butrol Represented by Formula 2

Gadolinium complex of 2,2,2-(10-1,3,4-trihydroxybutan-2-yl)-1,4,7,10-tetraazacyclododecane-1,4,7-triyl)triacetic acid (hereinafter, gadobutrol) of 200.0 g, tartaric acid of 241.02 g and purified water of 600 ml were put into a reactor, and heated to 85 to 95° C. to carry out reaction. After the end of reaction, the mixture was cooled to 20 to 30° C., and the produced solid was removed by filtration. The filtrate was subjected to a nano-filter and concentrated under reduced pressure, so that 2,2,2-(10-1,3,4-trihydroxybutan-2-yl)-1,4,7,10-tetraazacyclododecane-1,4,7-triyl)triacetic acid (butrol) of 105.4 g (yield 72.9%, purity 98% (HPLC)) was obtained.

[Example 2] Preparation of Calcobutrol Represented by Formula 3

2,2,2-(10-1,3,4-trihydroxybutan-2-yl)-1,4,7,10-tetraazacyclododecane-1,4,7-triyl)triacetic acid(butrol) of 50.0 g, calcium carbonate of 15.0 g and purified water of 200 ml were put into the reactor, and then heated to 85 to 95° C. to terminate the reaction, and cooled to 20 to 30° C. The filtrate was subjected to an activated carbon pad and concentrated under reduced pressure. 75 ml of purified water was added, heated to 85 to 95° C., maintained, and crystallized by adding 888.7 g of anhydrous Ethanol. This was refluxed for 1 hour, cooled to 0 to 10° C., and the producing crystals were filtered and washed with 177.7 g of anhydrous ethanol, and then dried, so that calcium complex of 2,2,2-(10-1,3,4-trihydroxybutane-2-yl)-1,4,7,10-tetraazacyclododecane-1,4,7-triyl) triacetic acid (hereafter, calcobutrol) of 44.4 g (yield 39.4%, purity 99.5% (HPLC)) was obtained.

The invention claimed is:
1. A method for producing calcobutrol comprising the steps of:
 obtaining butrol represented by following Chemical Formula 2 by reacting a gadobutrol represented by following Chemical Formula 1 and tartaric acid as a decom- plexing agent, wherein the butrol is filtered and purified using a nanofilter system; and
reacting calcium ions with the butrol to obtain a calcobutrol represented by following Chemical Formula 3,

[Chemical Formula 1]

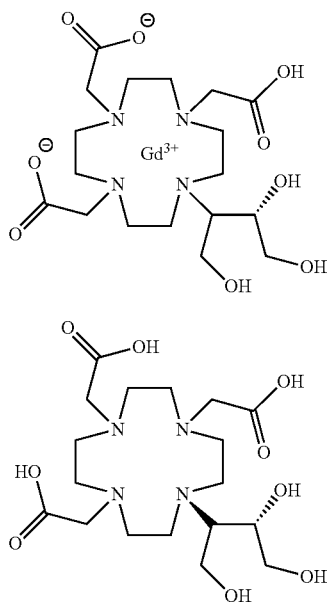

[Chemical Formula 2]

[Chemical Formula 3]

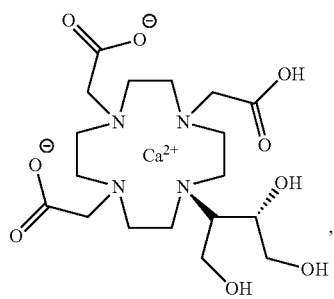

wherein the content of the decomplexing agent is 3.0 to 6.0 equivalents with respect to the gadobutrol and the calcium ion is selected from the group consisting of calcium carbonate, calcium hydroxide, calcium chloride and mixtures thereof, and the content of the calcium ion is 0.9 to 1.1 equivalents with respect to the gadobutrol.

2. The method as claimed in claim 1, wherein the calcobutrol is crystallized with ethanol anhydrous.

* * * * *